United States Patent [19]

Dretler

[11] Patent Number: 4,589,868
[45] Date of Patent: May 20, 1986

[54] EXPANDABLE DILATOR-CATHETER

[76] Inventor: Stephen P. Dretler, 172 Cochituate Rd., Wayland, Mass. 01778

[21] Appl. No.: 588,282

[22] Filed: Mar. 12, 1984

[51] Int. Cl.$^4$ ............................................. A61M 25/00
[52] U.S. Cl. ....................................... 604/96; 128/344
[58] Field of Search ......................... 604/96, 104, 102; 128/344, 207.14, 207.15

[56] References Cited

U.S. PATENT DOCUMENTS

| | | | |
|---|---|---|---|
| 3,394,705 | 7/1968 | Abramson | 604/96 X |
| 3,701,351 | 10/1972 | Harvey | 604/96 |
| 4,024,873 | 5/1977 | Antoshkiw et al. | 604/96 |
| 4,489,722 | 12/1984 | Ferraro et al. | 604/96 X |

*Primary Examiner*—Stephen C. Pellegrino
*Attorney, Agent, or Firm*—Fishman & Dionne

[57] ABSTRACT

A device capable of being used as both a dilator and catheter is presented. The dilator-catheter is comprised of an expandable housing having an interior wall and exterior wall with a space therebetween. A longitudinal cavity is provided through the housing, the cavity being defined by the interior wall. A preferably disc-shape retaining means is provided as an integral portion of the housing. The disc retainer is capable of greater relative expansion than the rest of the housing. Access means are also provided whereby any fluid, including air or liquid, may be delivered to the housing whereupon the entire housing will expand accordingly.

12 Claims, 4 Drawing Figures

U.S. Patent May 20, 1986 4,589,868
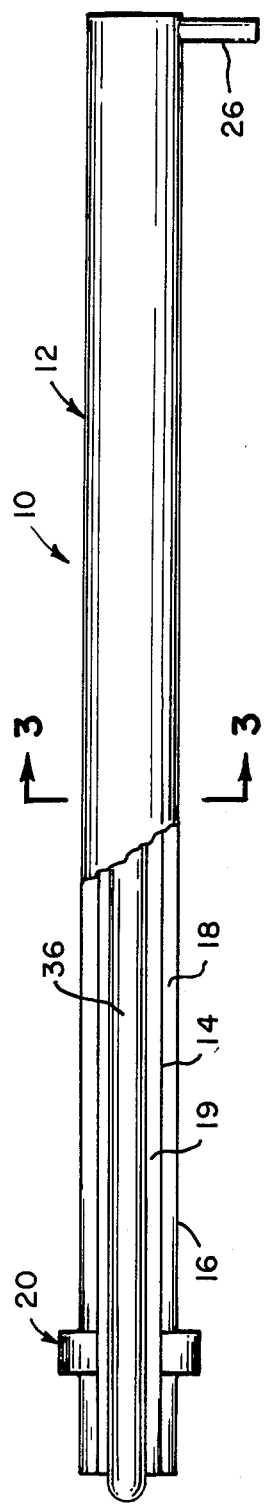
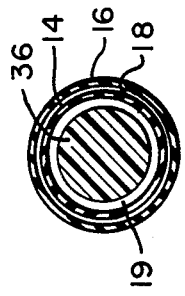
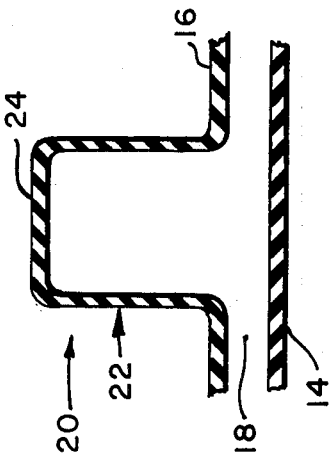
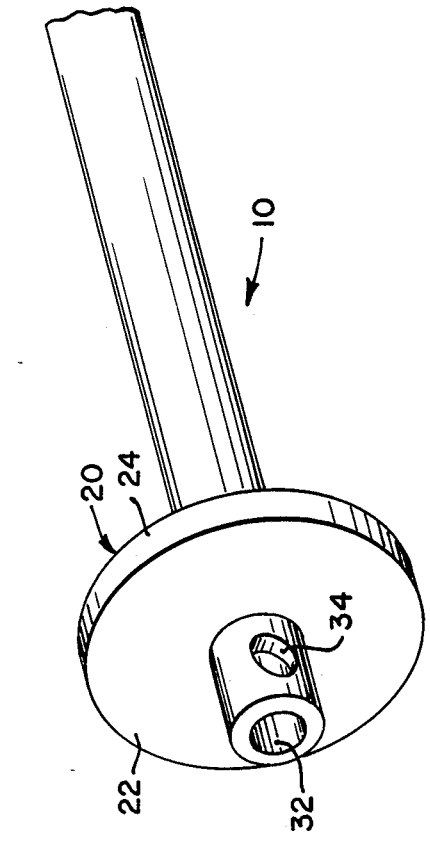

EXPANDABLE DILATOR-CATHETER

BACKGROUND OF THE INVENTION

This invention relates to a medical device capable of being used as both a dilator and a catheter. More particularly, this invention relates to a new and improved expandable dilator-catheter device having a structure analogous to a specially shaped inflatable balloon. It will be understood that while the present invention may be utilized in virtually any circumstance wherein a catheter or dilator is typically employed, it is particularly well-suited for urethral application. Accordingly, for the sake of clarity, the present invention and its developmental background will be principally discussed in terms of a urethra and bladder environment.

It is well recognized in the field of Urology that persons lose control of their urinary function. This loss of control may be temporary or permanent, depending upon the cause of the loss of urinary function. The bladder is a dome shaped container with muscular walls and which accepts urine from the kidneys for temporary storage. During normal voluntary urination, the muscles in the bladder wall contract and simultaneously the sphincter muscle surrounding the opening in the bladder which communicates with the urethra relaxes so that the urine stored in the bladder is released into the urethra and expelled from the body.

Since the loss of voluntary control over the urinary function is typically a secondary effect caused either by disease or trauma, it has become a well established medical practice to relieve the urinary drainage problem mechanically by means of the process of catheterization.

In the catheterization process, a tube or catheter is inserted into and through the urethra until the remote or distal end is located within the bladder, usually being disposed just past the sphincter muscle at the juncture of the bladder with the urethra. The near or proximal end of the tube remains outside of the body and there is thus provided a path or channel through which urine in the bladder can drain as the need arises. Once a catheter has been passed through the urethra and inserted into the bladder, it is generally necessary, in connection with the relevant disease and trauma conditions, to have the catheter retained in the urinary tract with the distal end of the catheter in the bladder, such retention being in the order of several days to several weeks without removal. Catheters which are designed for this use are called urinary retention catheters and are typically provided by including an inflatable balloon at the distal end of the catheter which is deflated during insertion of the catheter and which is inflated by passing a fluid, typically water or saline solution through a passage within the catheter, called an inflation lumen. Thereafter, fluid from the bladder drains through the main passage of the catheter, called the drainage lumen.

The basic design of commercially available prior art retention catheters has changed very little, and the well known Foley retention catheter is almost universally used by doctors, hospitals, nursing homes, etc. to alleviate loss of voluntary bladder control. Typical prior art catheters are usually formed of relatively thick walled construction so as to be insertable without buckling, have a rounded solid tip to prevent trauma to the delicate lining of the urethra, and have side openings adjacent the tip to communicate the interior of the bladder with the drainage lumen. The prior art catheters also have an inflatable balloon portion beyond the drainage opening in order to retain the catheter in place.

These catheters, and many more like them, are undesirable from the standpoint that considerable pain may be experienced in introducing a relatively wide, semi-rigid catheter into a relatively narrow urethra. Moreover, the inflatable balloon usually has a bulbous shape liquid-filled reservoir which is often uncomfortable and may lead to bladder spasms. Further, the small side openings can easily clog from clots of sediment material which collects in the bottom of the bladder. Still further, as a result of the solid tip, it is impossible to pass diagnostic or treatment instrumentation through the catheter for the purpose of inspecting or treating the interior of the bladder. The capability of inserting instrumentation through the catheter after it is in place is very important in the urological practice since prior treatment involves the use of anesthesia in order to insert steel tube instrumentation as has been the practice. Also, prior art catheters will often collapse when suction is applied, when, for example, blood clots are aspirated from the bladder.

Examples of prior art patents directed to catheters include, but are not limited to, U.S. Pat. Nos. 2,892,458, 2,936,761, 3,087,492, 3,292,627, and 3,394,705.

Similar to catheters, dilators are used extensively in the medical field for a variety of purposes. Generally, a dilator acts to progressively expand a narrow passageway in the body so that other instruments or the like may be passed therethrough. For example, in urology, and more specifically with urethral and ureteric lithiasis, the presence of calculus requires dilation in order to facilitate the intervention and the expulsion of the calculus formation. Currently, the treatment in such cases is to use a set of catheters, made of metal or other materials, which have gradually increasing diameters, so as to crush the calculus formation.

To produce the needed dilation, several methods are known in the medical art, including the laminae vegetales (still used, although infrequently), Champetier De Ribes's bladder, the Hegal dilators and various other dilators by now abandoned. The Hegal dilators are metal cones of progressively larger diameters, which are first introduced, left in situ for a while, and then extracted before applying cones of larger diameter.

The results obtained with these dilators are good, provided that they are handled by a skilled hand, thereby avoiding the risks of perforation and/or laceration as is the case whenever an object is introduced in tender parts of the human body. Unfortunately, the various dilating methods are not always entirely satisfactory, since they all exhibit limitations, potential hazards, and occasionally even applicational difficulties.

Clearly, it would be advantageous to combine the functions of a catheter and dilator in one medical instrument. A dilator-catheter of this type would preferably overcome the many deficiencies and problems related to known catheters and dilators as discussed above. Certain complicated attempts which have met limited success have been made toward this goal; for example, see U.S. Pat. Nos. 4,195,637, 4,271,839, 4,295,464, 4,318,410, and 4,338,942.

Accordingly, it is a principal object of the present invention to provide a dilation catheter device which overcomes the deficiencies of the prior art.

It is another object of the present invention to provide a medical device capable of performing both catheter and dilator functions, yet retaining a small diameter.

It is still another object of the present invention to provide a dilation catheter which will not collapse under an applied suction.

It is another object of the present invention to provide a dilation catheter having a more comfortable expandable retaining means.

It is yet another object of the present invention to provide a dilation catheter capable of expansion via both liquid and gaseous fluids.

DESCRIPTION OF THE DRAWINGS

These and other objects will become more apparent from the following detailed description taken in connection with the accompanying drawings wherein:

FIG. 1 is a front elevation view, partly broken away of a non-inflated dilation catheter in accordance with the present invention and having an obturator therein;

FIG. 2 is a perspective view of the dilation catheter of FIG. 1 after expansion thereof;

FIG. 3 is a cross-sectional elevation view of the dilation catheter of FIG. 1 along the line 3—3.

FIG. 4 is a cross-sectional elevation view showing a portion of the retaining means of the dilation catheter in accordance with the present invention.

DESCRIPTION OF THE PREFERRED EMBODIMENT

Referring first to FIG. 1, a dilator-catheter in accordance with the present invention is shown generally at 10. The dilator-catheter 10 is essentially comprised of a double layered cylindrical housing 12 having an inner or internal wall portion 14 and an outer or external wall portion 16 with an annular space 18 therebetween. A centrally located longitudinal cavity 19 is defined by the interior wall portion 14. The housing 12 has an annular disk section 20 at one end (distal end) thereof. The annular disk section 20 has a relatively larger diameter than the rest of the housing 12. The disk 20 includes opposing circular sidewalls 22 connected therebetween by annular ring 24.

The whole dilation catheter 10 is preferably comprised of a polyvinyl chloride (PVC) or similar plastic. Thus, it will be understood that the entire catheter 10 is analogous to an expandable or inflatable balloon and, more particularly, an elongated expandable tube. Accordingly, access means 26 are provided at the end of the catheter 10 farthest from the insertion end (proximal end) in order to accomplish the expansion thereof. Upon expansion, a fluid such as a liquid saline solution or, surprisingly, a gas (i.e., air) will be delivered through the access means 26 and into the space 18.

The disk section 20 of the dilation catheter 10 will act as a retaining means after insertion of the catheter 10 in, for example, a bladder. To accomplish this retaining function, in a preferred embodiment, the opposing exterior sidewalls 22 of the disk 20 will be thinner relative to the other wall portions 14 and 16 (see FIG. 4). As a consequence thereof, upon inflation of the housing 12, the sidewalls 22 of the disk 20 will undergo a proportionally greater degree of expansion than will the rest of the catheter (including the annular ring 24). It should be understood that while FIG. 4 shows the disk 20 having both exterior sidewalls 22 and interior sidewalls 28, the retaining disk 20 would be equally effective without the interior walls 28. Accordingly, in an embodiment which may have preferable manufacturing features, unlike FIG. 4, wall portion 14 will not protrude outwardly at the disk 20 area.

The dilation catheter 10 may be provided with any desired number of apertures or opening such as central opening 32 and side aperture 34 as shown in FIG. 3.

During actual use as, for example, a drainage tube application in a bladder, the present invention will be mounted via the longitudinal cavity 19 onto an obturator 36 such as shown in FIG. 1. Preferably, the obturator 36 will be comprised of a malleable material so that it can be selectively shaped to avoid obstructions and the like. After the obturator is inserted through the annular cavity 19, the distal end of the catheter 10 is extended through the urethra and into the bladder. At that point, air or another fluid may be introduced through the access means 26 located at the proximal end whereupon the catheter 10 will expand in place. The air or other fluid may be introduced by any conventional means. Note that the size of the dilation catheter, i.e., its transversed diameter, will be determined by the amount of fluid introduced into the space 18. Thus, the catheter 10 may be inserted without any fluid therein or partially inflated and then be expanded to the desired diameter. It will be understood, therefore, that one size catheter will fit virtually any urethra. In a preferred embodiment, the housing 12 having an obturator therein of 5 French (F) in diameter will be partially expanded to a diameter of 8F. After insertion of the disk 20 into the bladder, the catheter will be further expanded whereby the disk sidewalls 22 will increase to a radius of about one centimeter (FIG. 2) which is adequate to accomplish the desired retension function. At that point, the catheter is ready to be used as a bladder drainage tube.

Alternatively, the small size of the dilating catheter 10 may allow initial insertion via passing it through a standard urethroscope or other small lumen and then be expanded in place.

While the catheter 10 has been described above in terms of urethral application, it will be understood that the present invention may be used for any medical process wherein a catheter is employed. For example, longer balloon-type catheters made in accordance with the present invention may be used and left as in-dwelling stents, as, for example, in a ureter.

As mentioned earlier, the present invention may also be utilized as a dilator as well as merely a catheter or drainage tube. Thus, by progressively expanding the housing 12, the dilation catheter 10 can be used to dilate the particular passage (i.e., urethra) thereby creating a conduit for the passage of operating instruments into, for example, a bladder or kidney. The present invention is particularly well suited for dilating a stricture of the urethra before a TUR. It is believed that the dilation catheter 10 of the present invention can dilate a urethral up to at least 30F.

The dilation catheter of the present invention has many other features and improvements over the prior art. Thus, as the entire catheter is similar to a plastic balloon, after expansion thereof, the plastic will take on a certain amount of rigidity and will be less likely to collapse when suction is applied. This will permit blood clots to be aspirated without obstructing the lumen. Accordingly, the size of the catheter necessary to aspirate the clots can be relatively smaller than would be required in a single-walled catheter or a catheter comprised of latex.

Similarly, the catheter of the present invention may be used after an operation to drain blood clots in conjunction with a 3-way drainage apparatus as the interior diameter of the drainage apparatus will be large enough to accommodate clots.

Another important feature of the present invention is the fact that the expandable retention means 20 takes the shape of a disk or wafer rather than the usually bulbous shape liquid filled reservoir of the prior art. It is believed the present invention is more comfortable for the patient because of its disk shape. Also, because of the novel ability to be expanded by air, the air-filled disk will be lighter relative to a liquid filled disk thereby further increasing comfort. (Latex catheters cannot be air-filled as latex is permeable to air.) Since bladder spasms are one of the most common complication of catheters, changing the weight and shape of the prior art reservoir in accordance with the present invention should enormously decrease this problem.

The fact that the present invention may be used as both a dilator and catheter is an extremely desirable feature in terms of cost savings and increased applications. The small size of the present invention, prior to expansion, is also a desired feature. Thus, until the housing 12 is sufficiently inflated, it is capable of being delivered through a small lumen and then expanded in place. This will facilitate, for example, dilating a stricture of the urethra.

Having thus described the invention, what is claimed is:

1. A dilator-catheter comprising an elongated expandable tube for insertion into a body cavity, said tube having distal and proximal ends wherein the length of said tube is such that said distal end is disposed within a body cavity and the proximal end is disposed outside said body, said tube having an exterior wall and an interior wall in spaced relationship to one another thereby forming an annular space therebetween, expandable retaining means disposed near said distal end of said tube, said retaining means being defined by a portion of said exterior wall having substantially opposing side walls connected by an annular ring, said retaining means being formed by the expansion of said portion of said exterior wall of said tube, and means for providing fluid to said annular space for expanding said tube and said retaining means.

2. The device of claim 1 wherein:
said opposing sidewall portions of said exterior wall have a thickness less than the thickness of the remaining exterior wall.

3. The device of claim 1 including:
a portion of said interior wall having opposing side walls connected by an annular ring; said portion of said interior wall disposed across from said portion of said exterior wall.

4. The device of claim 3 wherein:
said opposing sidewall portions of said exterior wall have a thickness less than the thickness of the remaining exterior wall.

5. The device of claim 4 wherein:
said opposing sidewall portions of said interior wall have a thickness less than the thickness of the remaining interior wall.

6. The device of claim 1 wherein:
said retaining means has a disk shape.

7. The device of claim 1 including:
a longitudinal cavity defined by the interior wall of said expandable tube.

8. The device of claim 1 including:
at least one aperture between said longitudinal cavity and said exterior wall.

9. The device of claim 1 wherein:
said expandable tube is comprised of polyvinyl chloride.

10. The device of claim 1 wherein:
said fluid is a gas.

11. The device of claim 10 wherein:
said gas is air.

12. The device of claim 1 wherein:
said fluid is a liquid.

* * * * *